(12) United States Patent
Hirschel et al.

(10) Patent No.: US 11,058,822 B2
(45) Date of Patent: *Jul. 13, 2021

(54) DEVICE FOR ADJUSTING A DOSAGE WITH A LIMITING MECHANISM FOR A DEVICE FOR ADMINISTERING A PRODUCT

(71) Applicant: Ypsomed AG, Burgdorf (CH)

(72) Inventors: Jürg Hirschel, Bern (CH); Ulrich Moser, Heimiswil (CH)

(73) Assignee: Ypsomed AG, Burgdorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/867,041

(22) Filed: May 5, 2020

(65) Prior Publication Data

US 2020/0306454 A1 Oct. 1, 2020

Related U.S. Application Data

(63) Continuation of application No. 16/458,834, filed on Jul. 1, 2019, which is a continuation of application
(Continued)

(30) Foreign Application Priority Data

May 16, 2012 (CH) .................................. 00695/12

(51) Int. Cl.
*A61M 5/31* (2006.01)
*A61M 5/315* (2006.01)

(52) U.S. Cl.
CPC ...... *A61M 5/31541* (2013.01); *A61M 5/3155* (2013.01); *A61M 5/3156* (2013.01); *A61M 5/31551* (2013.01); *A61M 2005/3126* (2013.01)

(58) Field of Classification Search
CPC .......... A61M 5/31541; A61M 5/31551; A61M 5/3156; A61M 5/3155; A61M 2005/3126
See application file for complete search history.

(56) References Cited

U.S. PATENT DOCUMENTS

| 2,771,217 A | 11/1956 | Brown et al. |
| 2,991,662 A | 7/1961 | Johannes |

(Continued)

FOREIGN PATENT DOCUMENTS

| CH | 617857 A5 | 6/1980 |
| CH | 703993 A2 | 3/2012 |

(Continued)

OTHER PUBLICATIONS

U.S. Appl. No. 12/403,849, USPTO Non-Final Office Action dated Sep. 28, 2009, 21 pages.

(Continued)

*Primary Examiner* — Amber R Stiles
(74) *Attorney, Agent, or Firm* — Dorsey & Whitney LLP

(57) ABSTRACT

Dosing device for an administration device with a limiting mechanism, comprising a first limiting means with a first stop means, a second limiting means with a second stop means, wherein the second limiting means follows movements of the first limiting means during dosing movements with a defined transmission ratio, and wherein the first and the second stop means each describe a path curve by their movements in such a manner that the two path curves intersect in at least one point or come so close together that the stop means contact one another in a stop position, whereby a blocking of the movement of the limiting means relative to each other during dosing movements can be effected in that the respective path curves described by the first and second stop means are closed and can be run through preferably multiple times by the first stop means, by (Continued)

the second stop means or by both stop means until the stop means contact one another at the stop position.

22 Claims, 16 Drawing Sheets

Related U.S. Application Data

No. 15/694,226, filed on Sep. 1, 2017, now Pat. No. 10,518,035, which is a continuation of application No. 14/539,573, filed on Nov. 12, 2014, now Pat. No. 9,750,887, which is a continuation of application No. PCT/CH2013/000081, filed on May 13, 2013.

(60) Provisional application No. 61/647,851, filed on May 16, 2012.

(56) References Cited

U.S. PATENT DOCUMENTS

| | | |
|---|---|---|
| 3,082,914 A | 3/1963 | Wilbur |
| 3,202,151 A | 8/1965 | Kath |
| 3,411,366 A | 11/1968 | Alfonso |
| 4,583,978 A | 4/1986 | Porat et al. |
| 5,049,125 A | 9/1991 | Accaries et al. |
| 5,263,475 A | 11/1993 | Altermatt et al. |
| 5,514,097 A | 5/1996 | Knauer |
| 5,569,236 A | 10/1996 | Kriesel |
| 6,004,297 A | 12/1999 | Steenfeldt-jensen et al. |
| 6,123,684 A | 9/2000 | Deboer et al. |
| 6,221,053 B1 | 4/2001 | Walters et al. |
| 6,277,099 B1 | 8/2001 | Strowe et al. |
| 6,582,404 B1 | 6/2003 | Klitgaard et al. |
| 7,083,596 B2 | 8/2006 | Saied |
| 7,112,187 B2 | 9/2006 | Karlsson |
| 7,195,616 B2 | 3/2007 | Diller et al. |
| 7,645,265 B2 | 1/2010 | Stamp |
| 7,811,263 B2 | 10/2010 | Burren et al. |
| 8,834,431 B2 | 9/2014 | Kohlbrenner et al. |
| 9,114,211 B2 | 8/2015 | Moeller et al. |
| 9,750,887 B2 * | 9/2017 | Hirschel ............ A61M 5/3156 |
| 10,300,211 B2 | 5/2019 | Kohlbrenner et al. |
| 10,350,363 B2 | 7/2019 | Kohlbrenner et al. |
| 2004/0127858 A1 | 7/2004 | Bendek et al. |
| 2004/0260247 A1 | 12/2004 | Veasey et al. |
| 2005/0022806 A1 | 2/2005 | Beaumont et al. |
| 2005/0065477 A1 | 3/2005 | Jost |
| 2005/0080377 A1 | 4/2005 | Sadowski et al. |
| 2005/0197626 A1 | 9/2005 | Moberg et al. |
| 2005/0209570 A1 | 9/2005 | Moller |
| 2005/0261634 A1 | 11/2005 | Karlsson |
| 2006/0153693 A1 | 7/2006 | Fiechter et al. |
| 2006/0184117 A1 | 8/2006 | Knight et al. |
| 2006/0206057 A1 | 9/2006 | Deruntz et al. |
| 2006/0264839 A1 | 11/2006 | Veasey et al. |
| 2007/0016143 A1 | 1/2007 | Miller et al. |
| 2007/0021715 A1 | 1/2007 | Kohlbrenner et al. |
| 2007/0027430 A1 | 2/2007 | Hommann |
| 2007/0225657 A1 | 9/2007 | Hommann |
| 2008/0033369 A1 | 2/2008 | Kohlbrenner et al. |
| 2008/0051712 A1 | 2/2008 | Fiechter et al. |
| 2008/0051713 A1 | 2/2008 | Kohlbrenner et al. |
| 2008/0171997 A1 | 7/2008 | Kohlbrenner et al. |
| 2008/0234633 A1 | 9/2008 | Nielsen |
| 2008/0287883 A1 | 11/2008 | Radmer et al. |
| 2008/0306445 A1 | 12/2008 | Burren et al. |
| 2009/0048561 A1 | 2/2009 | Burren et al. |
| 2009/0247959 A1 | 10/2009 | Kohlbrenner et al. |
| 2009/0247960 A1 | 10/2009 | Kohlbrenner et al. |
| 2009/0254035 A1 | 10/2009 | Kohlbrenner et al. |
| 2009/0254044 A1 | 10/2009 | Kohlbrenner et al. |
| 2009/0275916 A1 | 11/2009 | Harms et al. |
| 2009/0299297 A1 | 12/2009 | Moeller et al. |
| 2012/0283647 A1 * | 11/2012 | Cronenberg ...... A61M 5/31541 604/207 |
| 2014/0350484 A1 | 11/2014 | Kohlbrenner et al. |
| 2017/0035973 A1 | 2/2017 | Schenker et al. |
| 2017/0043098 A1 | 2/2017 | Kohlbrenner et al. |
| 2017/0361024 A1 | 12/2017 | Hirschel et al. |
| 2019/0022332 A1 | 1/2019 | Kohlbrenner et al. |
| 2019/0247587 A1 | 8/2019 | Kohlbrenner et al. |
| 2019/0321558 A1 * | 10/2019 | Hirschel ............ A61M 5/31541 |

FOREIGN PATENT DOCUMENTS

| | | |
|---|---|---|
| CH | 706567 A2 | 11/2013 |
| DE | 20112501.3 U1 | 12/2002 |
| DE | 10229122 A1 | 2/2004 |
| DE | 102004063644 A1 | 7/2006 |
| DE | 102004063647 A1 | 7/2006 |
| EP | 0554995 A1 | 8/1993 |
| EP | 0554996 A1 | 8/1993 |
| EP | 0554996 B1 | 10/1996 |
| EP | 1681070 B1 | 2/2009 |
| EP | 1516638 B1 | 1/2010 |
| EP | 2814547 A1 | 12/2014 |
| EP | 2918298 A1 | 9/2015 |
| EP | 3603703 A1 | 2/2020 |
| GB | 862641 A | 3/1961 |
| WO | 0041754 A1 | 7/2000 |
| WO | 0119434 A1 | 3/2001 |
| WO | 02053214 A1 | 7/2002 |
| WO | 2002053214 | 7/2002 |
| WO | 2004002556 A1 | 1/2004 |
| WO | 2004078226 A2 | 9/2004 |
| WO | 2004078239 A1 | 9/2004 |
| WO | 2004078240 A2 | 9/2004 |
| WO | 2004089450 A1 | 10/2004 |
| WO | 2006024461 A1 | 3/2006 |
| WO | 2006039930 A1 | 4/2006 |
| WO | 2006077466 A2 | 7/2006 |
| WO | 2006084876 A1 | 8/2006 |
| WO | 2006086983 A1 | 8/2006 |
| WO | 2006089768 A1 | 8/2006 |
| WO | 2006130100 A1 | 12/2006 |
| WO | 2008031237 A1 | 3/2008 |
| WO | 2011039207 A1 | 4/2011 |
| WO | 2013170392 A1 | 11/2013 |
| WO | 2014117944 A1 | 8/2014 |
| WO | 2016016184 A1 | 2/2016 |
| WO | 2020026050 A1 | 2/2020 |

OTHER PUBLICATIONS

"Link to Opposition of EP2814547", https://register.epo.org/application?number=EP13724506&Ing=en&tab=doclist, accessed Apr. 26, 2017, 3 pages.
"U.S. Appl. No. 61/647,851, filed May 16, 2012 in the name of Jurg Hirschel".
"U.S. Appl. No. 12/403,849", Applicant's Response to Non-Final Office Action dated Sep. 28, 2009, submitted on Feb. 26, 2010, 14 pages (w/EFS Acknowledgment).
"U.S. Appl. No. 12/403,849", USPTO Final Office Action dated May 27, 2010, 10 pages.
"International Preliminary Report on Patentability", Application No. PCT/CH2007/000241, dated Apr. 7, 2009, 15 pages.
"International Preliminary Report on Patentability", Application No. PCT/CH2013/000081, dated Nov. 18, 2014, 6 pages.
"International Search Report", Application No. PCT/CH2007/000241, dated Sep. 6, 2007, 6 pages.
"International Search Report and Written Opinion", Application No. PCT/CH2013/000081, dated Sep. 23, 2013, 11 pages.
"Written Opinion of the International Searching Authority", Application No. PCT/CH2007/000241, dated Mar. 15, 2009, 12 pages.
International Preliminary Report on Patentability received for International Application No. PCT/IB2019/055547 dated Feb. 11, 2021, 8 pages.

(56) References Cited

OTHER PUBLICATIONS

International Search Report and Written Opinion received for International Application No. PCT/IB2019/055547, dated Jul. 31, 2019, 9 pages.

* cited by examiner

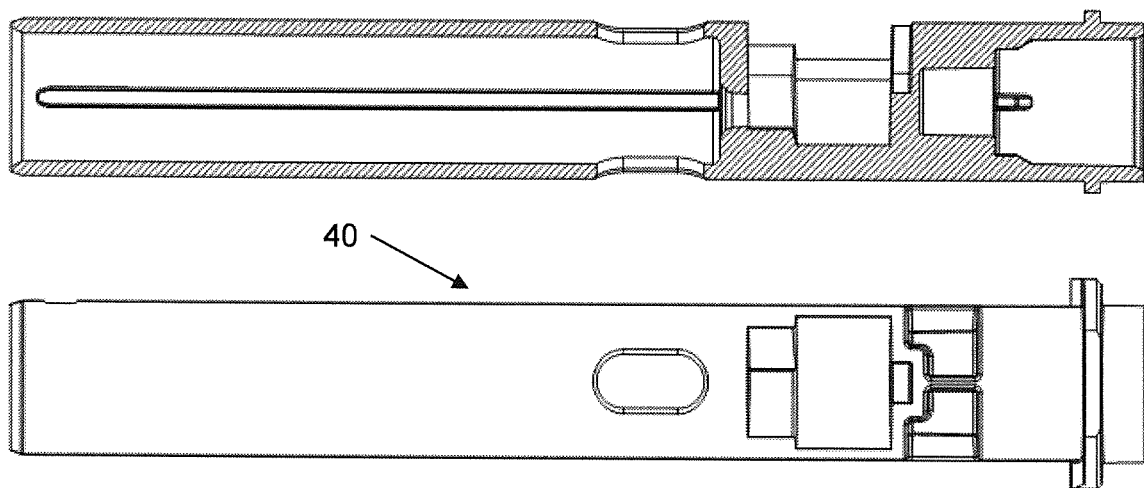
Fig. 16
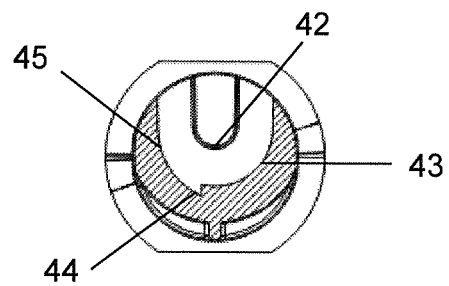
Fig. 17
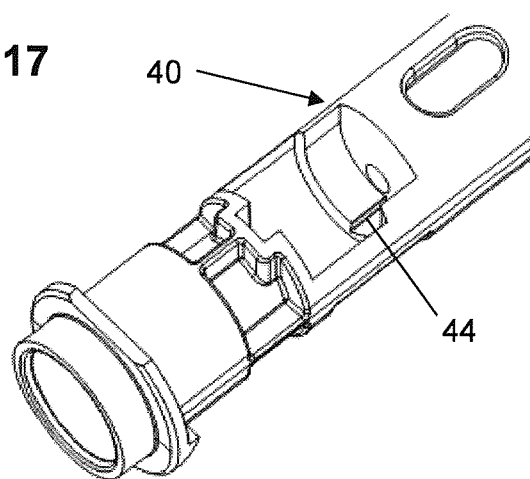

DEVICE FOR ADJUSTING A DOSAGE WITH A LIMITING MECHANISM FOR A DEVICE FOR ADMINISTERING A PRODUCT

CROSS-REFERENCE TO RELATED APPLICATIONS

This application is a continuation of U.S. patent application Ser. No. 16/458,834, filed Jul. 1, 2019, which is a continuation of U.S. patent application Ser. No. 15/694,226, filed Sep. 1, 2017, now U.S. Pat. No. 10,518,035, which is a continuation of U.S. patent application Ser. No. 14/539,573 filed Nov. 12, 2014, now U.S. Pat. No. 9,750,887, which is a continuation of International Patent Application No. PCT/CH2013/000081 filed May 13, 2013, which claims priority to Swiss Patent Application No. 00695/12 filed May 16, 2012 and U.S. Patent Application No. 61/647,851 filed May 16, 2012, the entire contents of each of which are incorporated herein by reference.

BACKGROUND

The invention relates to an improved device for adjusting a dosage in a device for administering a product, for example an injection syringe for insulin in the form of a pen-shaped syringe for self-administration of insulin, referred to as a pen. The invention further relates to a limiting mechanism that prevents the adjustment of a dosage to be administered past a predetermined value. As an example for the invention, but not restrictive to the applications in administration devices, embodiments of such devices are described in the published patent application CH 703993 A2, which is herewith incorporated in full by reference.

In administration devices with product containers, e.g., an inserted cartridge that contains a product for several administrations, it is sometimes desirable to prevent a dosage from being preselected that exceeds the amount of product remaining in the cartridge. If such a dosage could be preselected, the user would assume that a corresponding dosage can be administered, whereas in fact only a part is administered. This is undesirable or even dangerous depending on the situation.

A means for solving this problem known from prior art is to count or measure the total as the sum of the administered dosages, with a limit stop preventing a further ejection or dosage selection as soon as the total corresponds to the volume nominally contained in the cartridge.

A drive mechanism for medicine administration devices is described in the published patent application WO 2004/078226 for example. This drive mechanism contains a housing, a dosage-setting sleeve and a two-part piston. In one embodiment, a driver sleeve moves downward along an inner part of the piston rod when a dosage is selected. The distance traveled corresponds to the ejection stroke of the piston necessary for the dosage. When a subsequent dosage is selected, the driver sleeve moves farther along the piston rod. The position of the driver sleeve thus corresponds to the quantity of medication still contained in the cartridge. When the driver sleeve reaches the end of the thread on the inner part of the piston rod and therefore can no longer rotate, this corresponds to an empty cartridge.

Another example is described in the published U.S. Pat. No. 6,582,404, which shows a limiting mechanism for medication administration devices that prevents setting a dosage which exceeds the amount remaining in the cartridge. The administration device comprises a dosage-setting member which is moved away from a fixed limit stop by rotation relative to a driver when setting a dosage. The dosage-setting member is connected to the driver in such a manner that the former can be turned in one direction without moving the latter. The dosage is administered by turning back the dosage-setting member and thereby moving the driver. The rotating driver causes an ejection motion of the piston rod. The driver is provided with a track, the length of which corresponds to the quantity of medication contained in the cartridge. A track follower, which is connected to the dosage-setting member, runs in this track. Every time a dosage is selected, the track follower moves farther in the track. When the track follower reaches the end of the track, the dosage-setting member cannot be turned further and setting a dosage beyond the amount still remaining in the cartridge is prevented.

Another example of such a device is described in EP 0554996 and shows an injection device for administering liquids such as insulin into bodily tissue. This injection device contains a dosage-setting mechanism having a 1-ring and a 10-ring. A transmission member is provided for selectively coupling the one ring to the other so that they turn together only in selected sections during the dosage-setting. The set dosage is displayed by means of digits on the rings. The injection device further comprises a dosage-limiting mechanism, which limits the movement of a guide spindle for the intended piston motion in the cartridge, wherein projections in the plunger reach the end of grooves along the guide spindle and prevent a further movement. The dosage-limiting mechanism is provided separately from the dosage-setting mechanism.

Finally, WO 2006/086983 shows an example of a dosage-setting device for self-injection devices with a dosage-limiting mechanism having two rotating parts, wherein the first part turns continually while setting a dosage and the second part only turns part of the time by a selective coupling device after a defined rotational position has been reached. This has the effect that the second part turns discontinuously over a smaller angle than the first part. The rotation of the second part is then limited by a limit stop fixed to the housing, which prevents a dosage setting exceeding the remaining amount still present in the cartridge.

A disadvantage of dosage-setting devices for self-injection devices known from the prior art with a dosage-limiting mechanism is that such devices require considerable space and/or coupling mechanisms, which require control and negatively influence the limitation.

The problem of the present invention is to create a device for setting a dosage in an injection or infusion device for administering a product having a limiting mechanism that reliably, simply and space-effectively prevents the setting of a dosage to be administered beyond a predetermined value and also overcomes other disadvantages known from the prior art.

This problem is solved by the subject matter with the characteristics of Claim 1.

Additional advantageous embodiments follow from the dependent claims.

SUMMARY

Various indications of directions and positions are made in the present description, which will be briefly explained at this point. "Axial orientation" means an orientation along the longitudinal axis of an administration device or of some other device. "Distal" refers to the end of the administration device at which the product exits. Accordingly, "proximal" refers to the opposite end of the administration device. "In the distal direction" means viewed in the direction of the distal end and "in the proximal direction" analogously means viewed in the direction of the proximal end.

The invention relates, for example, to an improved injection device for administering a fluid product. Such an injection device comprises a housing with a receptacle for the product, a conveying unit for conveying the product and a dosing device for setting a product dosage to be administered and for displaying the set product dosage. The housing forms a receptacle for the product, preferably a receptacle for a container filled with the product. This container can be a cartridge for example. The conveying unit comprises a piston rod, which is movable relative to the housing in a conveyance direction in order to eject the set product dosage in a conveyance stroke corresponding to the set product dosage. The conveyance stroke is a translational movement of the piston rod, preferably a linear pushing movement. In a preferred embodiment, a movable piston of the container constructed as a cartridge is displaced in the conveyance stroke. The conveying unit further comprises a guide element, which guides the translational movement of the piston rod. In a preferred embodiment, the guide element is constructed as a longitudinal guide for the piston rod, fixed relative to the housing, so that the piston rod can be displaced relative to the guide element but cannot be rotated. The conveying unit further comprises a drive element that is engaged with the piston rod. The drive element in a preferred embodiment is constructed as a threaded nut, the inside thread of which is brought into engagement with a corresponding outside thread applied to the outer surface of the piston rod. The threaded nut is preferably mounted in the housing rotatably, but axially fixedly. In a possible preferred embodiment, the following kinematic arrangement results for the conveying mechanism of the conveying unit: a rotation of the axially fixed threaded nut relative to the piston rod results in an axial movement of the piston rod, because it cannot rotate relative to the housing due to the longitudinal guide. In other embodiments, likewise preferred, the kinematic arrangement can also be inverted. This is effected via a so-called kinematic inversion, wherein the threaded nut is rotationally fixed relative to the housing and the longitudinal guide is rotatable relative to the housing and also movably mounted. If the longitudinal guide is rotated with this kinematic inversion, then the piston rod screws due to the threading of the threaded nut, which is rotationally fixed relative to the housing in this case.

The dosing device of the injection device comprises a dosage-setting member, preferably a dosing sleeve, which is in threaded engagement with the inside of the housing. A grippable element, which allows setting of a desired dosage by the user, is mounted at the proximal end of the dosage-setting member. When the dosage to be administered is increased, the dosage-setting member preferably undergoes a turning movement out of the injection device. To administer the set dosage or to reduce a dosage that may have been set too high, the dosage-setting member can then be screwed back into the injection device. In another preferred embodiment, there is a non-self-locking threaded connection between the housing and the dosage-setting member configured as a dosing sleeve, so that the dosing sleeve can be screwed back into the injection device by exerting axial forces.

The dosing device further comprises a coupling device, which can operatively connect the dosing device to the conveying device. The coupling device is designed in such a manner that a dosage to be administered can be set and/or corrected independently of the conveying device and that the dosing device can be selectively operatively coupled to the conveying device during the administration of the dosage, so that a movement of the dosing device is transferred completely or proportionally to the conveying device as an ejection movement. For example only the rotational proportion of a screw movement of a dosing sleeve, or alternatively only the axial displacement thereof, can be transferred to the conveying device. In one embodiment, the coupling device comprises a coupling sleeve with a coupling surface, wherein the coupling surface has engagement elements. The dosage-setting member constructed as a dosing sleeve has a counter-coupling surface with counter-engagement elements. The coupling surface and the counter-coupling surface can be brought into engagement with one another by a coupling movement and a relative movement between the coupling and the dosing sleeve can thus be suppressed.

The dosing device further comprises an ejection button, which is movably mounted at the proximal end of the dosing device. In a preferred embodiment of the dosage-setting member as a dosing sleeve, the ejection button is mounted coaxially with the dosing sleeve at the proximal end thereof. Preferably, the button is rotatable with respect to the dosing sleeve and is mounted with a certain axial movability. In a preferred embodiment, the coupling sleeve is also arranged coaxially with the dosing sleeve, the coupling sleeve preferably being arranged at least in part inside the dosing sleeve. In this embodiment, the coupling surface is arranged as an annular flange on the outer surface of the sleeve in the proximal area thereof. Complementarily the counter-coupling surface is also arranged on the inside of the dosing sleeve. In one possible embodiment, the engagement elements and the counter-engagement element are oriented axially relative to the injection device so that in this case the coupling movement is an axial movement. For example, the coupling engagement can be created by pressing the ejection button. The arrangement of the dosing sleeve, coupling sleeve and ejection button can further comprise a spring, which holds the coupling surface and the counter-coupling surface in engagement. The dosing sleeve and the coupling sleeve move jointly axially during a dosing movement, wherein a rotation relative to one another is possible as long as the ejection button is not pressed and therefore the coupling is not locked.

In a preferred embodiment, the coupling sleeve is rotationally secured relative to the threaded nut, but axially movable. This embodiment allows an axial movement of the coupling sleeve relative to the threaded nut. If the coupling is locked by pressure on the ejection button and the dosing sleeve is screwed into the injection device, then the coupling sleeve follows this movement. Due to the rotational locking of the threaded nut, the rotation is only transmitted to the threaded nut, and consequently the piston rod is axially moved.

In order to ensure that the drive element constructed as a threaded nut can rotate only in the direction that results in a movement of the piston rod in the ejection direction, i.e., in the direction causing an ejection, a so-called reverse rotation lock is preferably provided between the housing and the threaded nut. This can be a radially directed or an axially directed reverse rotation lock. The reverse rotation lock is preferably constructed by a form-fitting means in such a manner that a rotation of the threaded nut contrary to the ejection direction is completely blocked. For rotation in the ejection direction, the reverse rotation lock preferably has a certain resistance, also known as reluctance, due to a frictionally engaging means, which must be overcome in order to bring about a movement of the threaded nut. This is advantageous in order to prevent an undesired ejection when correcting an excessively high dosage. Preferably, the rotation resistances of the reverse rotation lock and the coupling are matched to one another.

According to a first aspect, the dosing device according to the invention has a limiting mechanism containing the following parts:

a first limiting means with a first stop means adapted in such a manner that the limiting means follows a movement of the dosage-setting member during the dosing movement a second limiting means with a second stop means adapted in such a manner that the second limiting means continuously follows a movement of the first limiting means during the dosing movement proportionally with a defined transmission ratio, and during an ejection movement does not undergo any relative movement with respect to the first limiting means.

The first and the second stop means each describe a path curve in such a manner by their movements that the two path curves intersect in at least one point or come so close together that the stop means strike against one another, whereby a blocking of the movement and the dosing movement can be effected. Preferably the stop means move at identical speed on different-length path curves, or at different speeds on equal-length path curves, wherein closed path curves can be passed through by one or both stop means, preferably several times, or partially until the stop means strike one another at a limit stop position.

In a preferred embodiment, the first limiting means can be constructed preferably on an inner axial wall section of the dosing sleeve as a circumferential toothing consisting of teeth and teeth interstices. The first stop means is constructed as a wedge which fills out a tooth interstice in a part of the wall section and thus interrupts the circumferential toothing. This section is referred to as a stop zone and the section with freely running toothing as a drive zone.

The second limiting means can be constructed as a sleeve-like stop wheel with distally and proximally projecting axial ends of a rotational shaft, wherein the rotational shaft is held by spoke means, which can also be constructed as a continuous wall in the interior of the stop wheel. Circumferential toothing consisting of teeth and teeth interstices is constructed on an outer wall section of the stop wheel. The second stop means is formed on the outer wall section of the stop wheel by a rib that extends one of the teeth in the axial direction. The second limiting element or stop wheel is also axially arranged in such a manner that its circumferential toothing meshes with the circumferential toothing of the first limiting means in the area of the drive zone, and the rib is moved in the area of the stop zone. The shaft ends are rotatably received by bearing points in the coupling sleeve so that the stop wheel, operatively connected positively in the toothing, can rotate about its own axis parallel to the common rotational axis of the dosing sleeve and the coupling sleeve.

In a preferred embodiment, the first stop means moves on a circular path curve during a dosing movement, due to the relative movement of the dosing sleeve and the coupling sleeve, and the second stop means moves on a path curve that can be circular. If there is a lack of relative movement of the dosing sleeve and the coupling sleeve during an ejection movement, the stop means do not move against one another on these curves. Suitable selection of the dimensions and the transmission ratio can have the effect that the stop means pass through their path curves several times until, starting from a stop position, they again contact one another at the stop position. These distances or this angle of rotation from stop position to stop position can be referred to as periods.

Such a period results mathematically from the least common multiple (LCM) of the numerator and denominator of the transmission ratio. Therefore, it turns out that the period can advantageously have large values if at least the numerator or the denominator is selected as a prime number. Thus appropriately long paths or angles of rotation can be dimensioned or limited with simultaneously high resolution and a compact construction, because the path curves can be run through several times. For example, by suitable selection of a starting position inside a period, any desired distance of rotation that must be run through until the stop position is reached can be defined. By suitable selection of the initial position for the stop wheel, the dosage limitation can be programmed to any desired number of fractions of tooth pitches or rotations inside a period, without structural changes to the design form being necessary. In a preferred embodiment, such a distance can correspond to the amount of medication nominally contained in the cartridge. Every time a dosing movement takes place, the stop means run relative to one another on their path curves and can thus reach their stop position. Thereby the dosing sleeve cannot turn farther in the dosage-increasing direction and a dosage setting exceeding the remainder still present in the cartridge is prevented. In a preferred embodiment this is achieved directly by virtue of the fact that, by contacting one another, the stop means prevent further movement of the two limiting means in the limit stop direction. On the other hand, it is possible to leave the stop position at any time by reversing the movement, in which case the dosing sleeve turns in the dosage-reducing direction.

In another preferred embodiment according to a second aspect, such a prevention of further movement of the two limiting means can also be done indirectly by means of a force that appears in the mutual striking of the two stop means against an elastic restoring force and/or via a gearing means that brings a first limit stop means on the coupling sleeve into engagement with a second limit stop means on the second limiting means. In a preferred embodiment, a radial limit stop can be formed, preferably integrally, on the second limit stop means, on an outer wall section of the stop wheel. This axial section is called a limit stop zone. The force acting between the two stop means is able to deform the rotational axis and/or the spoke means on the stop wheel elastically, whereby the stop wheel is translated or pivoted transversely to its axis of rotation. In the process, the second limit stop means comes into operative connection with the first limit stop means, which is applied in the area of the limit stop zone on the coupling sleeve. This operative connection can be configured as a friction fit or a form fit, as a counter-radial stop on the coupling sleeve in a preferred embodiment, and prevents further relative rotation of the stop wheel in the dosage-increasing direction relative to the coupling sleeve, which in turn cannot turn in the dosage-increasing direction due to the reverse rotation lock. In another preferred embodiment, the second limit stop means can also be supported in a transverse guide in the stop wheel movably in the transverse direction and fixed rotationally and axially relative to the rotational axis of the stop wheel, and can be held in its normal position by a spring means. This second limit stop means extends axially past the limit stop zone and the stop zone. The second stop means is applied in the area of the stop zone on the second limit stop means opposite the radial limit stop, which can extend past the limit stop zone. Instead of returning the second limit stop means from its stop position into its normal position by means of a spring means, this can be effected in another preferred embodiment by a gear guidance, which borders on the radial limit stop as a curved surface on the coupling sleeve in the limit stop zone and moves the second limit stop means radially in its transverse guide during return rotation of the stop wheel, in which case the dosing sleeve turns in the dosage-reducing direction.

As an additional safety aspect, the axial movement of the piston rod, the conveyance stroke, can be blocked when the maximum conveyable product quantity has been reached. For this purpose, at least one limit stop, which comes into engagement with a counter-limit stop on the drive element as soon as the maximum conveyable product amount has been conveyed out of the injection device, can be arranged at the proximal end of the piston rod. The limit stop and the counter-limit stop can act radially, i.e., perpendicular to the longitudinal axis of the injection device, due to end of threads. Alternatively, the limit stop and the counter-limit stop can also act axially, i.e., parallel to the longitudinal axis of the injection device. Axial and radial actions can also be combined in advantageous embodiments.

Further aspects and arrangements of embodiments according to the invention are presented in the descriptions of the figures.

BRIEF DESCRIPTION OF THE DRAWINGS

FIG. 16 is a longitudinal section and side view of the coupling sleeve in the third embodiment.

FIG. 17 is a longitudinal section and side view of the coupling sleeve in the third embodiment with a first limiting means.

DETAILED DESCRIPTION

Figure 1:
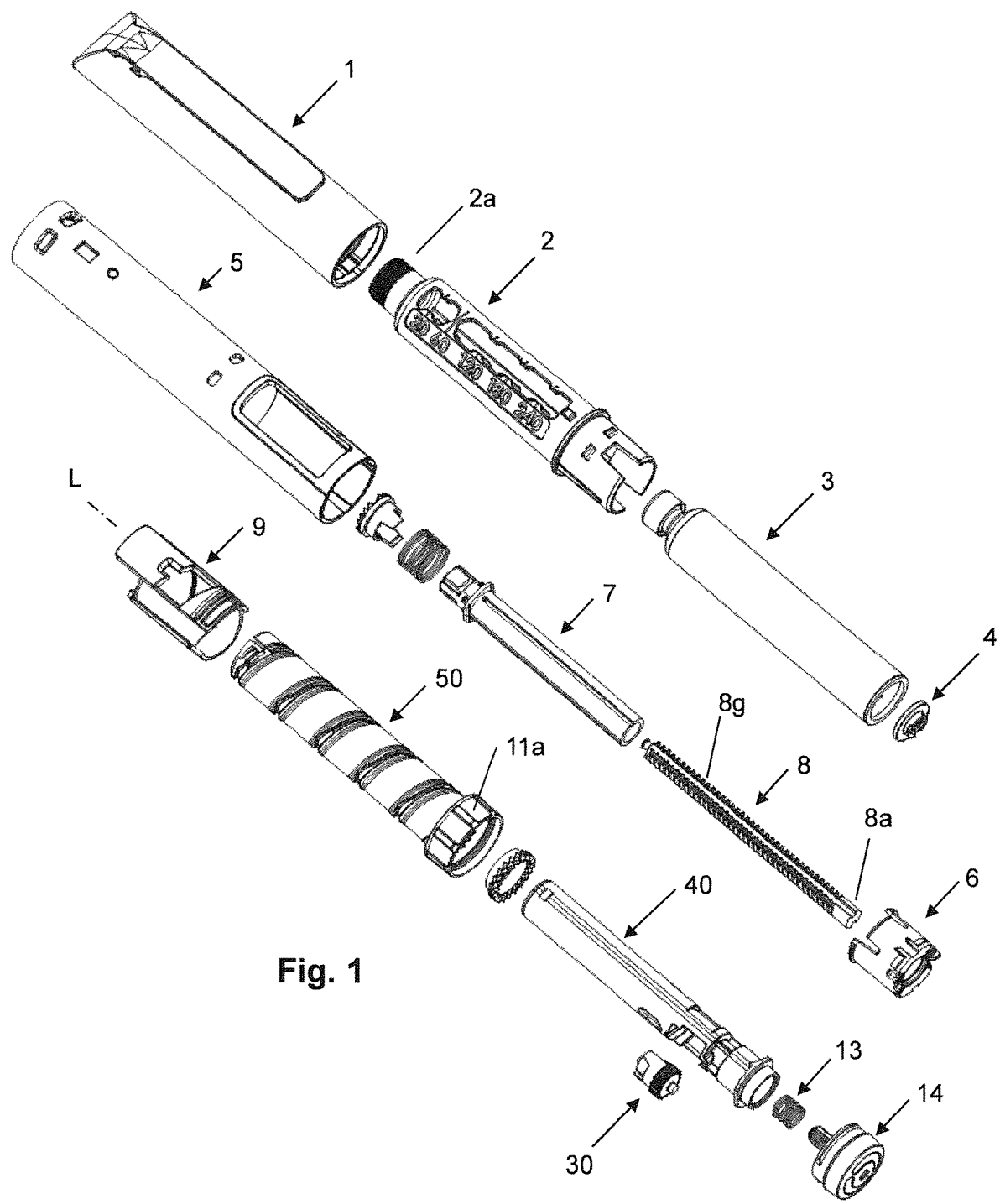
FIG. 1 is an exploded view of the individual parts of a first embodiment of an injection device according to the invention.
Figure 2:
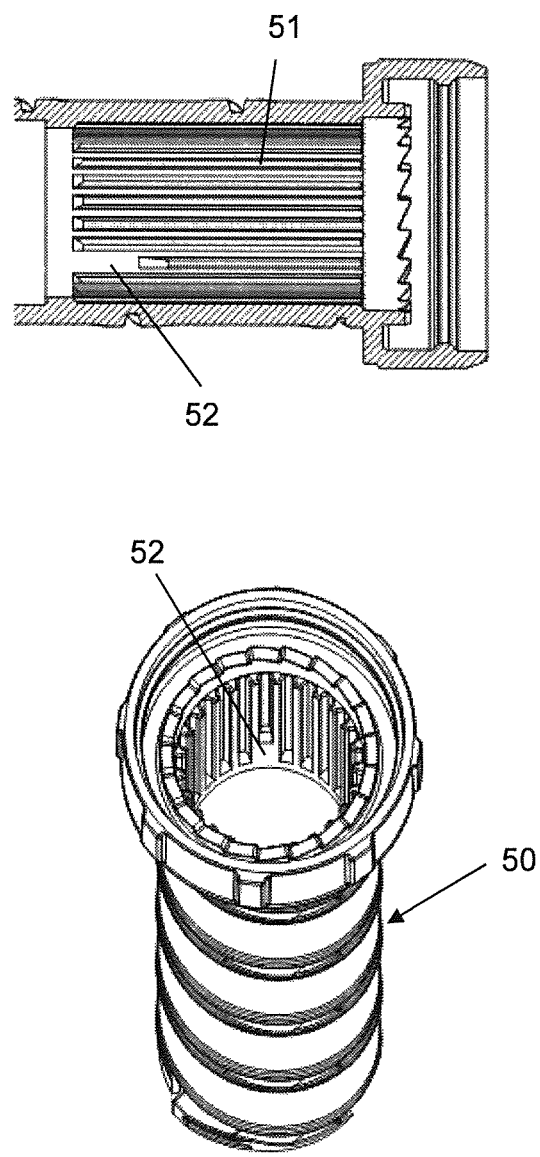
FIG. 2 is a longitudinal section and side view of the dosing sleeve in the first embodiment with a first limiting means.
Figure 3:
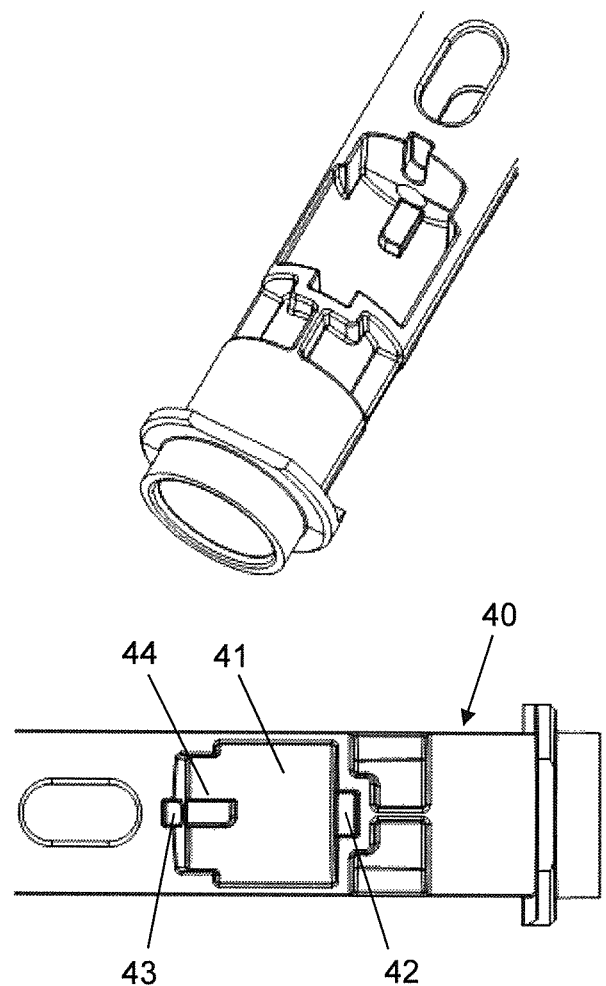
FIG. 3 is a side views of the coupling sleeve in the first embodiment.
Figure 4:
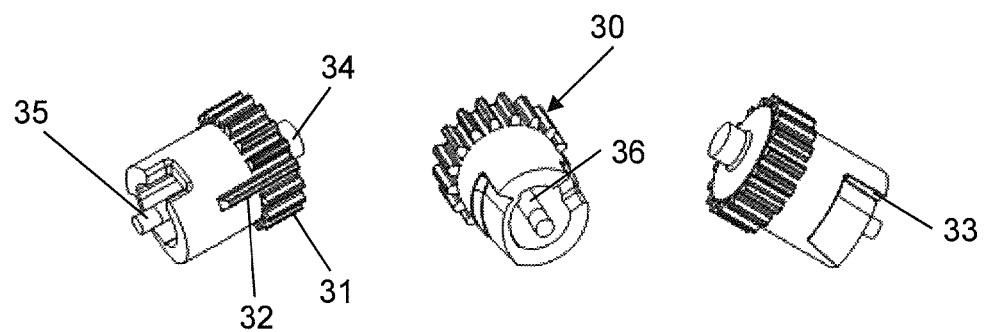
FIG. 4 is a side views of the second limiting means in the first embodiment in the form of a stop wheel.
Figure 5A:
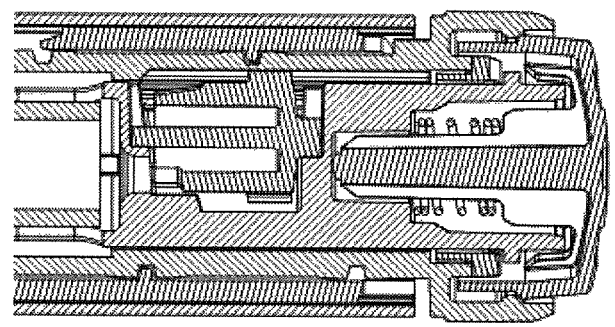
FIGS. 5a and b are longitudinal sections of the limiting mechanism in the first embodiment in a normal position and a stop position.
Figure 5B:
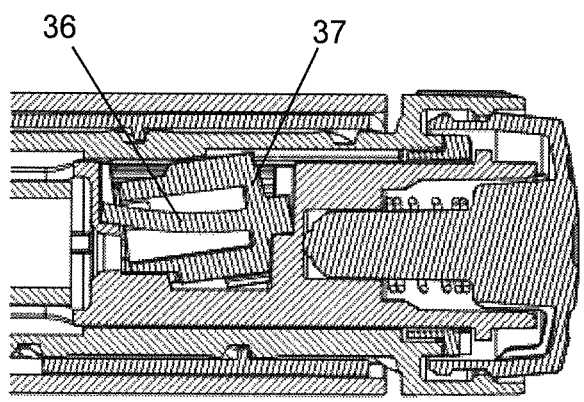
Figure 6:
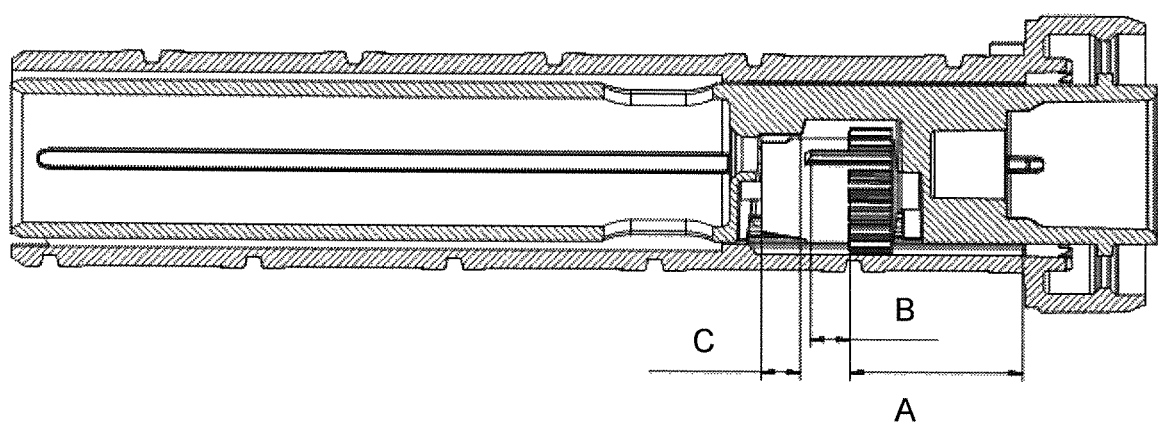
FIG. 6 is a longitudinal section of the limiting mechanism in the first embodiment with axial drive, stop and limit stop zones.
Figure 7:
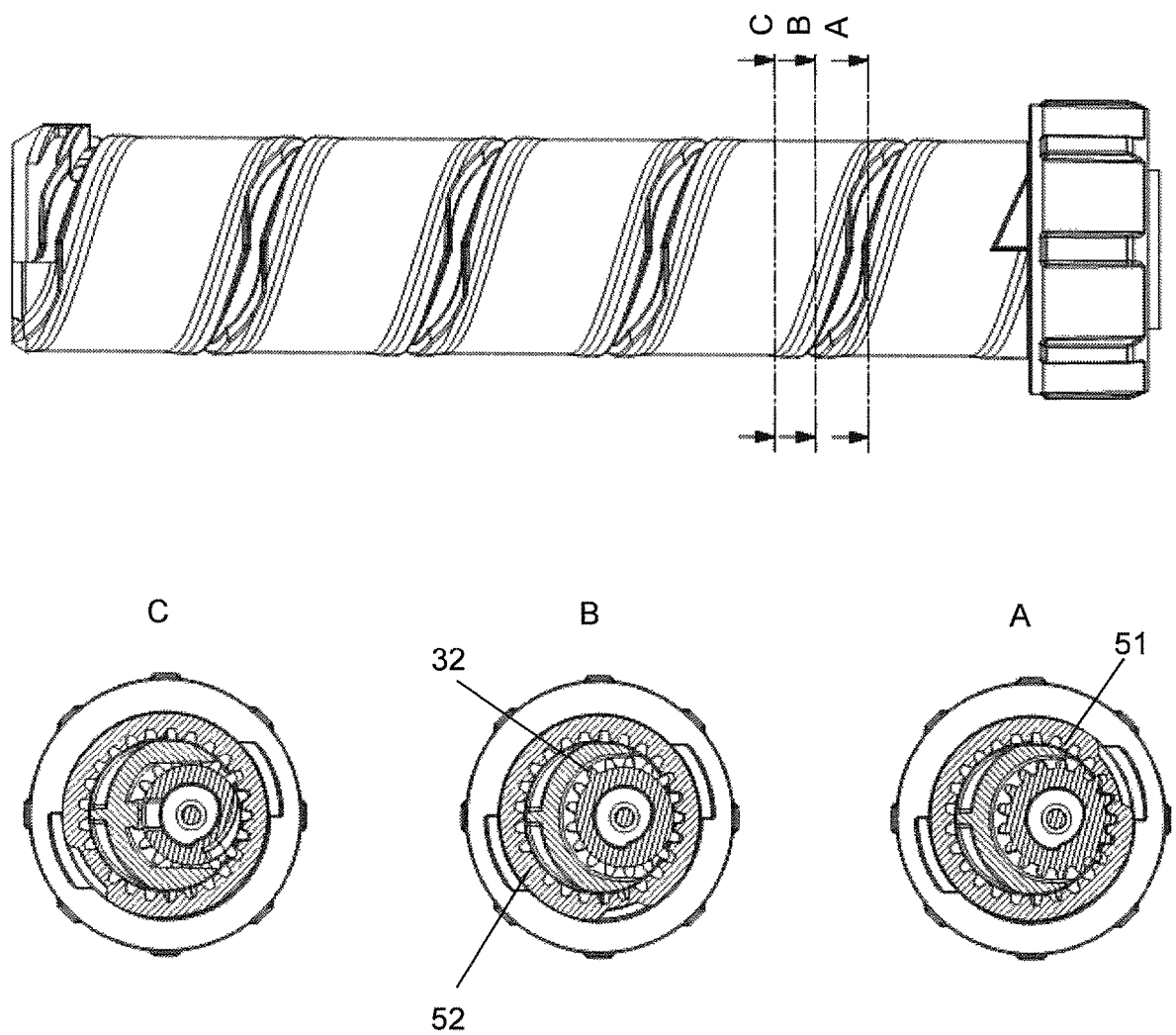
FIG. 7 is a side view of the limiting mechanism in the first embodiment and cross sections in axial drive, stop and limit stop zones in a normal position.
Figure 8:
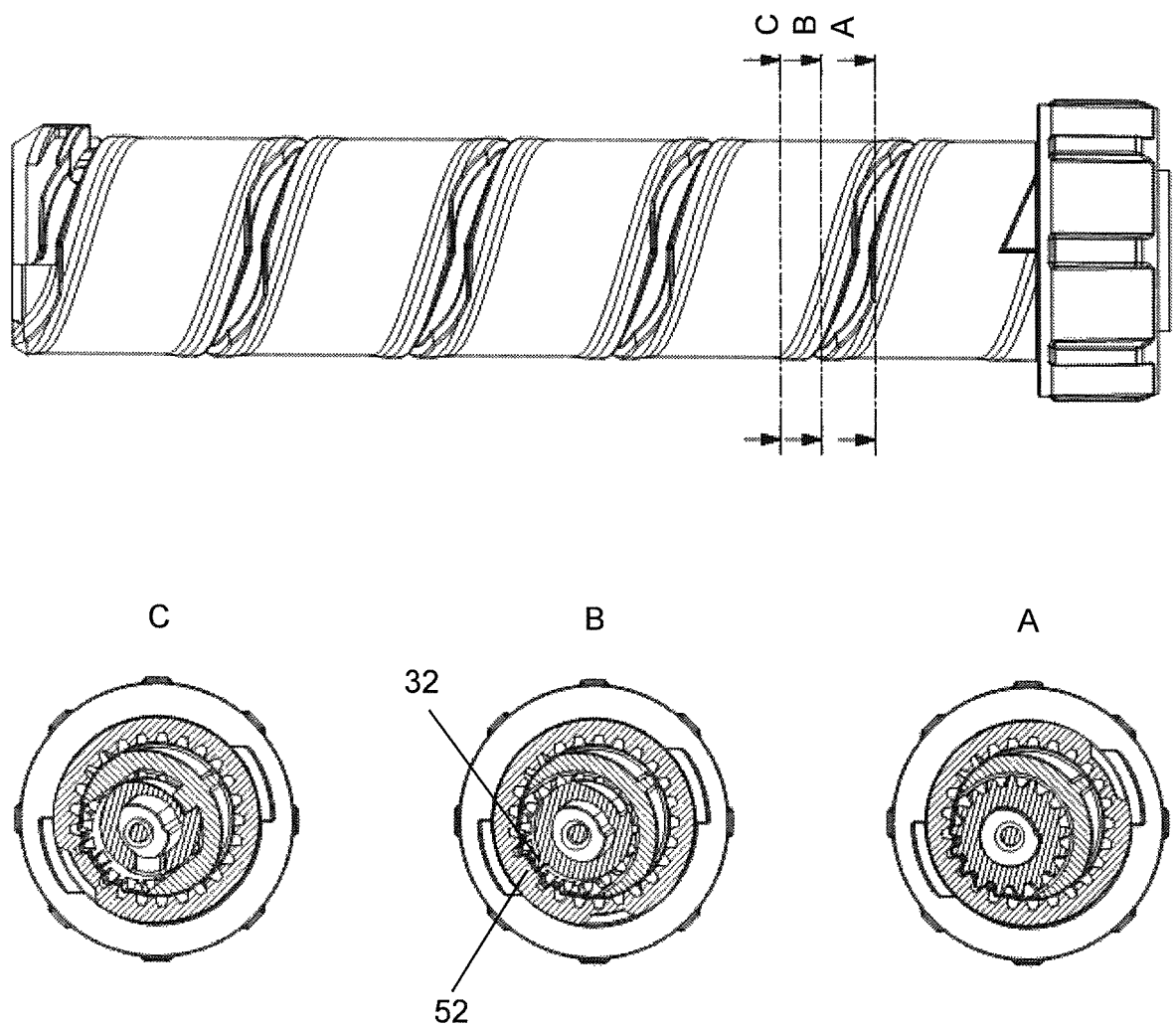
FIG. 8 is a side view of the limiting mechanism in the first embodiment and cross sections in axial drive, stop and limit stop zones in a stop position.
Figure 9A:
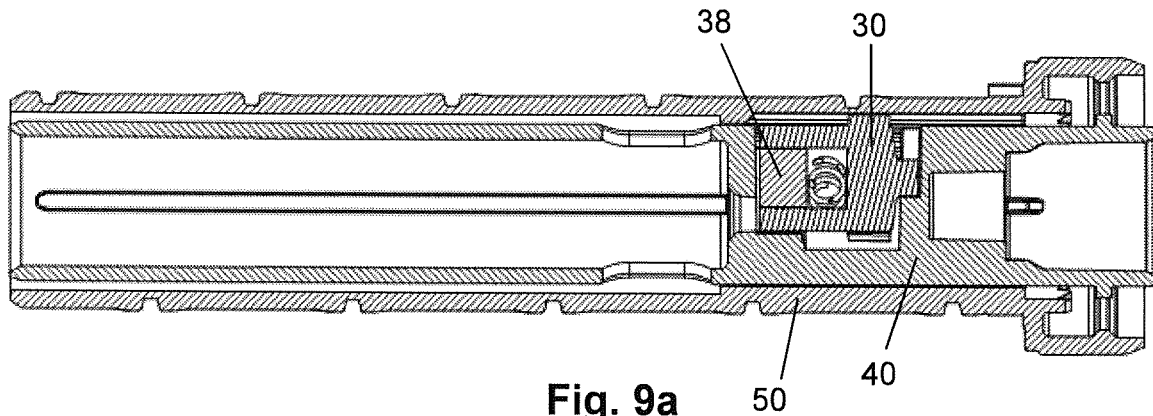
FIGS. 9a and b are longitudinal sections of the limiting mechanism in a second embodiment in a normal position and a stop position.
Figure 9B:
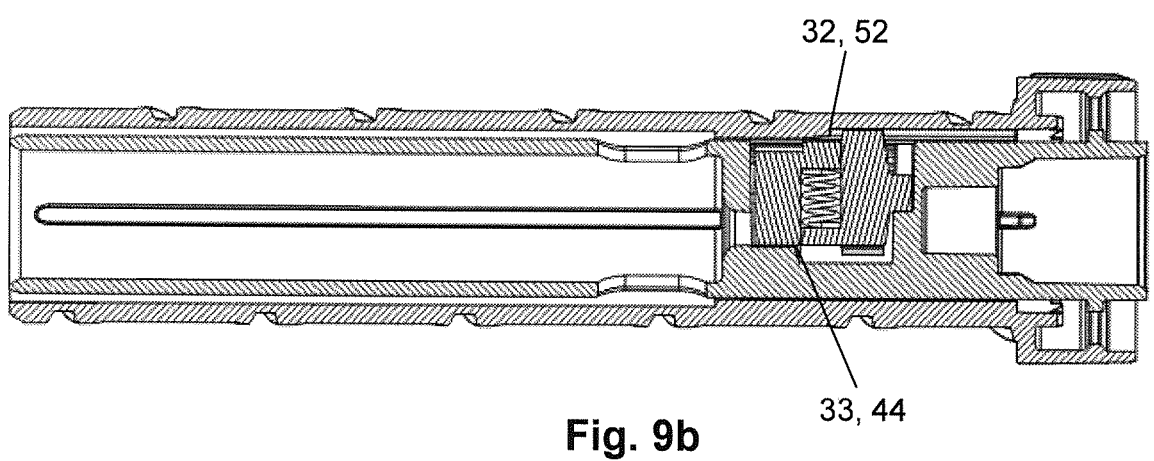

FIGS. 1-8 show a first embodiment of the device according to the invention installed in an injection device for the sake of example. FIG. 1 shows an exploded view of the individual parts of a first embodiment of an injection device according to the invention. FIG. 2 shows a longitudinal section and a side view of the dosing sleeve in the first embodiment with the first limiting means. FIG. 3 shows side views of the coupling sleeve in the first embodiment. FIG. 4 shows side views of the second limiting means in the first embodiment in the form of a stop wheel. FIG. 5 shows longitudinal sections of the limiting mechanism in the first embodiment in a normal position and a stop position. FIG. 6 shows a longitudinal section of the limiting mechanism in the first embodiment with axial drive, stop and limit stop zones. FIG. 7 shows a side view of the limiting mechanism in the first embodiment and cross sections in the axial drive, stop and limit stop zones in a normal position. FIG. 8 shows a side view of the limiting mechanism in the first embodiment and cross sections in the axial drive, stop and limit stop zones in a stop position.

The first embodiment is designed as a so-called single-use pen. That is to say, the ejection device is issued to the user fully assembled, i.e., with product to be administered. Before use, the user need only expel the air from the injection device, also known as priming. The typical course of the injection process may be as follows: the user removes the protective cap 1 from the injection device and mounts an injection needle (not shown) on the needle holder 2a. Now the dosage can be adjusted via the rotary knob 11a. For this purpose, the rotary knob 11a is turned so that the dosing sleeve 50 is screwed out of the injection device. The dosing sleeve 50 is screwed out of the injection device until the desired dosage is displayed in the window of the threaded sleeve 9. If an excessively high dosage is inadvertently set, the dosage can be corrected by turning the rotary knob in the opposite direction, whereby the dosing sleeve 50 is screwed back into the housing. The dosing device limits the maximum adjustable dosage to a predetermined value. If there is an attempt to screw the dosing sleeve out of the housing past this value, a radial limit stop on the dosing sleeve 50 and a counter-limit stop on the threaded sleeve 9 prevent further rotation by mutual interaction.

During the dosing and correction movements, the dosing sleeve 50 rotates relative to the coupling sleeve 40. The coupling sleeve 40 is held rotationally fixedly in a form fit or friction fit against the housing 5 by a reverse rotation lock (not shown, e.g., applied to the threaded nut 7 and housing 5), for example by means of latch and snapping means. If the desired dosage has been set, the injection needle can be inserted at the intended position on the body of the user. Then the user pushes the ejection button 14 in the distal axial direction and thus blocks a relative rotation between the coupling sleeve 40 and the dosing sleeve 50. In case of further pressure in the distal axial direction, the dosing sleeve begins to move back into the housing in a screwing motion. Because of the established rotational lock between the dosing sleeve 50 and the coupling sleeve 40, the coupling sleeve 40 carries out the same movement as the dosing sleeve 50. Because the coupling sleeve 40 is permanently rotationally locked to the axially stationary threaded nut 7, the rotational movement of the dosing sleeve 50 is transmitted to the threaded nut 7. No axial forces are transmitted to the threaded nut 7, because the coupling sleeve 40 is mounted axially movably on the threaded nut 7. Thus the rotating threaded nut 7 produces an axial movement of the threaded rod 8 in the distal direction, wherein the latter is guided axially and locked rotationally in the housing 5. The flange 4 acts on the plug of the cartridge and pushes it, corresponding to the displacement of the threaded rod 8 in the distal direction as well, wherein the previously set dosage can be ejected or administered. At the end of the administration, when the dosing sleeve has been completely screwed back into the housing, radial stops on the dosing sleeve 50 and the threaded sleeve 9 prevent further ejection and overrotation of the dosing device.

The limiting device according to the invention ensures that the most recently set dosage can be completely ejected or injected.

For this purpose, the dosing sleeve 50 has coaxially applied toothing 51, which can extend axially over the three axial sections, drive zone A, stop zone B and limit stop zone C. Circumferential toothing is formed at least in the drive zone A. A first stop means is formed as a stop wedge 52 in the axial extension of a tooth interstice of the circumferential toothing 51 in the stop zone B. As described above, the coupling sleeve 40 is inserted coaxially into the dosing sleeve 50. Preferably, the coupling sleeve 40 has a lateral cutout 41, which extends at least in certain sections across the three sections, drive zone A, stop zone B and limit stop zone C, and in which the stop wheel 30 is inserted. The rotational shaft 36 of the wheel, connected by spoke means 37 to the wheel, is rotatably received at its proximal shaft end 34 in the proximal bearing 42, and at its distal shaft end 35 in the distal bearing 43 of the coupling sleeve 40. At least in one area of the drive zone A, circumferential toothing 31 with 17 teeth, for example, which mesh with the circumferential toothing 51 with 25 teeth, for example, on the dosing sleeve 50, is formed on the stop wheel 30. The transmission formed in this manner sets the stop wheel 30 into rotation whenever the dosing sleeve 50 and the coupling sleeve 40 rotate relative to one another about their common axis L. The rotational shaft 36 of the stop wheel 30 is offset parallel to this axis L. A second stop means is formed as a stop rib 32 in the axial extension of the tooth in the circumferential toothing 31, at least in the stop zone B. In the limit stop zone C, a first limit stop means is formed in the cutout 41 of the coupling sleeve 40 as a radially acting limit stop 44, which can be brought into engagement with a second limit stop means constructed as a radially acting counter-limit stop 33 in the limit stop zone C on the stop wheel 30. This engagement takes place by pivoting the stop wheel 30 out of a normal position into a stop position against the elastic force of its rotational shaft 36 and/or the elastic force of its spoke means 37. The engagement prevents further rotation of the stop wheel 30 in the dosage-increasing direction. Because a rotation of the coupling sleeve 40 relative to the housing 5 in the dosage-increasing direction is blocked by the reverse rotation lock (not shown), the dosing sleeve 50 can also not be rotated further in the dosage-increasing direction by the interlinkage formed by the toothing 31 and the toothing 51. Conversely, the engagement and this blocking due to the restoring force of the rotational shaft are released as soon as the stop rib 32 detaches from the stop wedge 52 during a rotation of the stop wheel 30 in the dosage-reducing direction and the pivoted stop wheel 30 can move back into its normal position. The stop wheel 30 is pivoted only when the stop rib 32 strikes the stop wedge 52. With 25 teeth for toothing 51 and 17 teeth for toothing 31 for example, and with a maximally selected starting position, this occurs after 25 times 17=425 tooth pitches, which corresponds to one period. The stop wheel 30 turns 25 times and the dosing sleeve 50 turns 17 times in this example until the stop rib 32 strikes the stop wedge 52 and the resulting transverse force brings the first and second limit stop means into engagement, as already described. By suitable selection of the initial position of the stop wheel 30, the dosage limitation can be programmed to any desired number and fractions of tooth pitches or rotations inside the period, without structural changes having to be made to the design. For example, one tooth pitch can correspond to one insulin unit IU. and the stop wheel can be initially inserted at the point corresponding to 125 tooth pitches per period, so that limitation occurs after a total of 300 preselected or ejected IU.

Figure 10:
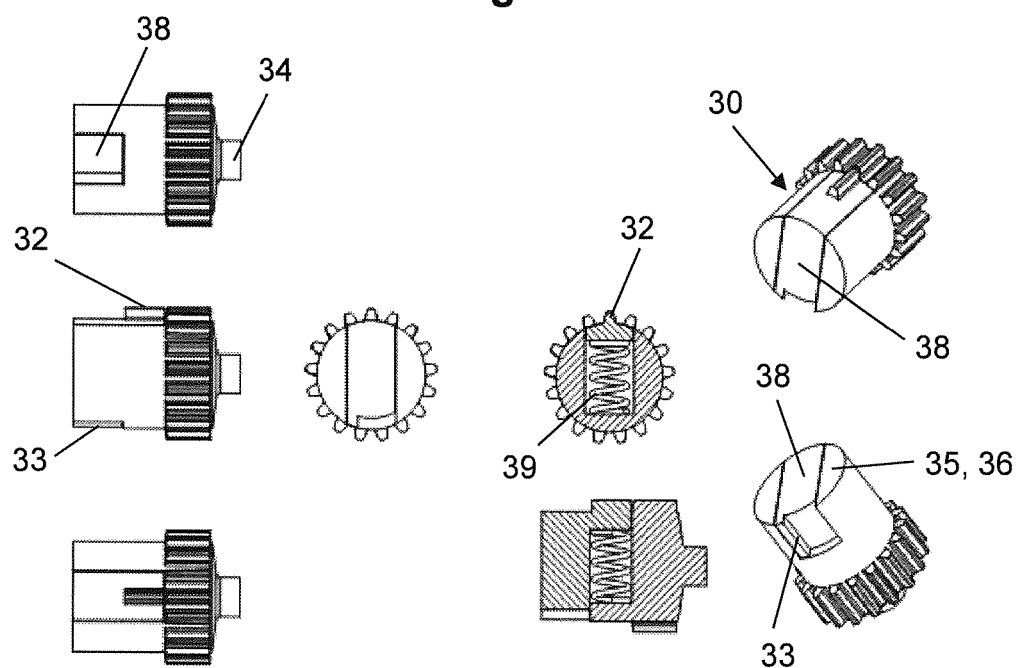
FIG. 10 is a side views and cross sections of the second limiting means in the second embodiment in the form of a stop wheel with a transversely movable second limit stop means and a spring means.
Figure 11:
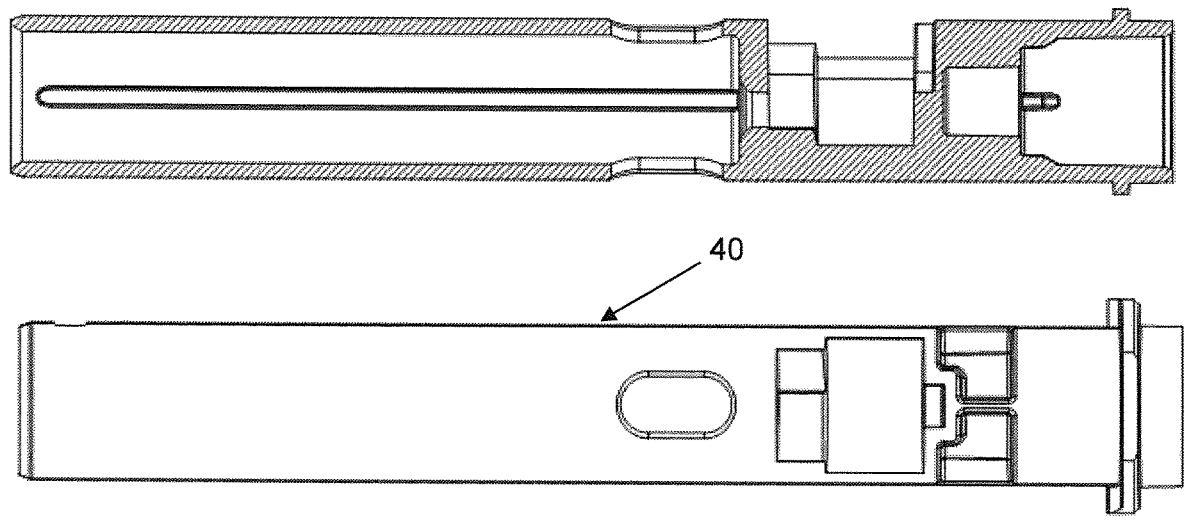
FIG. 11 is a longitudinal section and a side view of the coupling sleeve in the second embodiment
Figure 12:
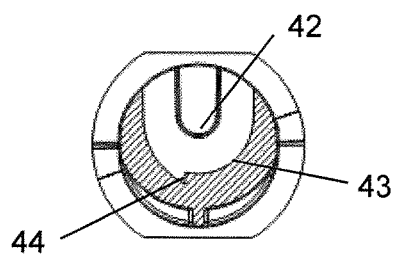
FIG. 12 is a cross section and a side view of the coupling sleeve in the second embodiment with a first limit stop means.
Figure 12:
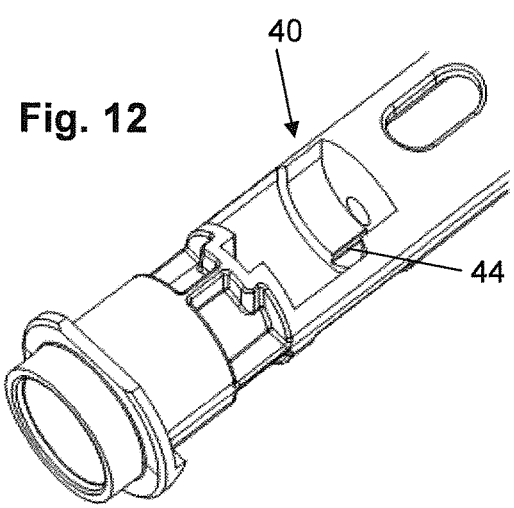
Figure 13:
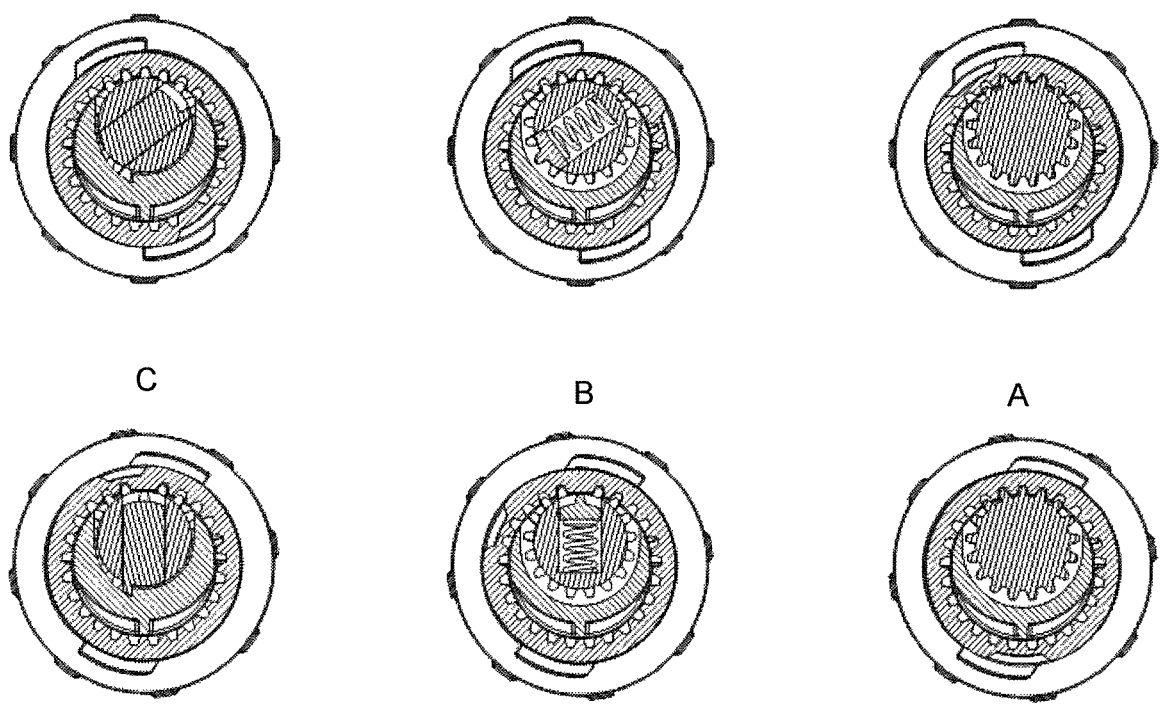
FIG. 13 is a cross sections of the limiting means in the second embodiment in axial drive, stop and limit stop zones in a normal position and a stop position.
Figure 14A:
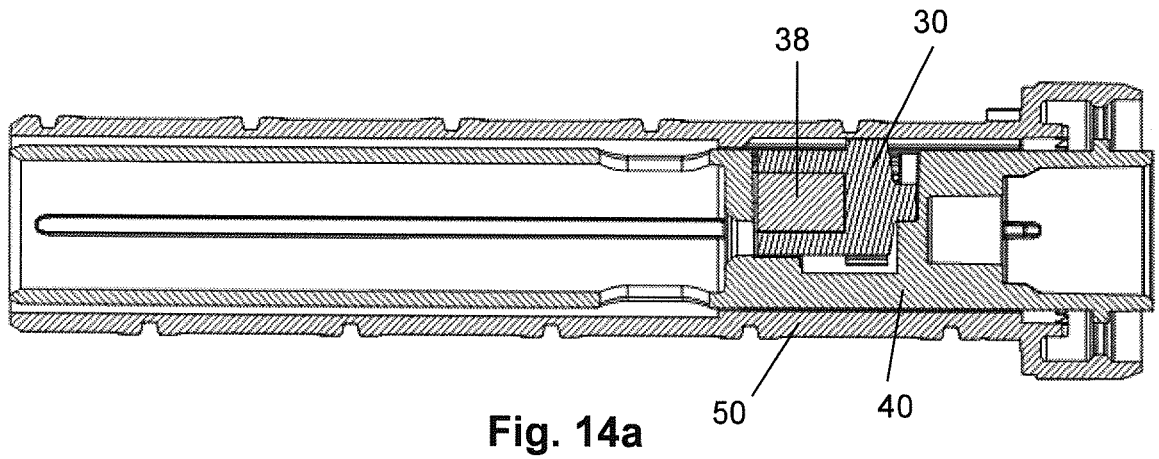
FIGS. 14a and b are longitudinal sections of the limiting mechanism in a third embodiment in a normal position and a stop position.
Figure 14B:
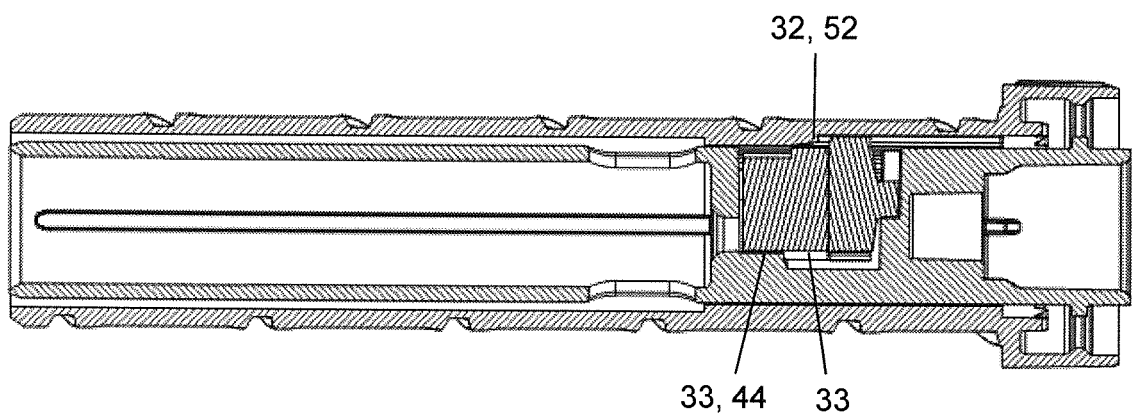

FIGS. 9-13 show a second embodiment of the device according to the invention installed as an example in an injection device similar to FIG. 1. FIGS. 9a and b show longitudinal sections of the limiting mechanism of the second embodiment in a normal position and in a stop position. FIG. 10 shows side views and cross sections of the second limiting means in the second embodiment in the form of a stop wheel with a transversely movable second limit stop means and spring return. FIG. 11 shows a side view and a longitudinal section of the coupling sleeve in the second embodiment. FIG. 12 shows a side view and a cross section of the coupling sleeve in the second embodiment with a first limit stop means. FIG. 13 shows cross sections of the limiting mechanism in the second embodiment in axial drive, stop and limit stop zones in a normal position and a stop position.

The application and function of the second embodiment correspond to the first embodiment apart from the following modifications made for the sake of example. The stop wheel 30 is designed with a rigid rotational shaft 36, the wheel and the shaft preferably being solidly integrated, and is rotatably received at the proximal shaft end 34 in the proximal bearing 42 and at its distal shaft end 35 in the distal bearing 43 of the coupling sleeve 40. In the area of the stop zone B and the limit stop zone C, a transverse guidance groove with inserted slider 38 is provided in the rotational shaft 36 or in the stop wheel 30. In the slider 38 or in the rotational shaft 36, a space is opened in the interior in the area of the stop zone, in which a spring means 39, preferably a compression spring in the form of a helical spring, is seated. This spring means holds the slider 38 in its transversal normal position. In this position, the stop rib 32 on a face of the slider 38 can mesh with toothing 51 optionally formed in the area of the stop zone, so long as the stop rib 32 does not strike the stop wedge 52. If that is the case, the slider is shifted transversely to the rotational shaft against the elastic force of the spring means 39 into a stop position. The counter-limit stop 33 formed on the side face of the slider 38 opposite the stop rib 32 as a second limit stop means is thereby brought into engagement with the limit stop 44 applied as a first limit stop means to the coupling sleeve 40. The engagement prevents further rotation of the stop wheel 30 in the dosage-increasing direction. Conversely, this engagement is released by the restoring force of the spring means 39 as soon as the stop rib 32 detaches from the stop wedge 52 during a rotation of the stop wheel 30 in the dosage-reducing direction and the slider 38 can move back into its normal position due to the force of the spring means 39.

Figure 15:
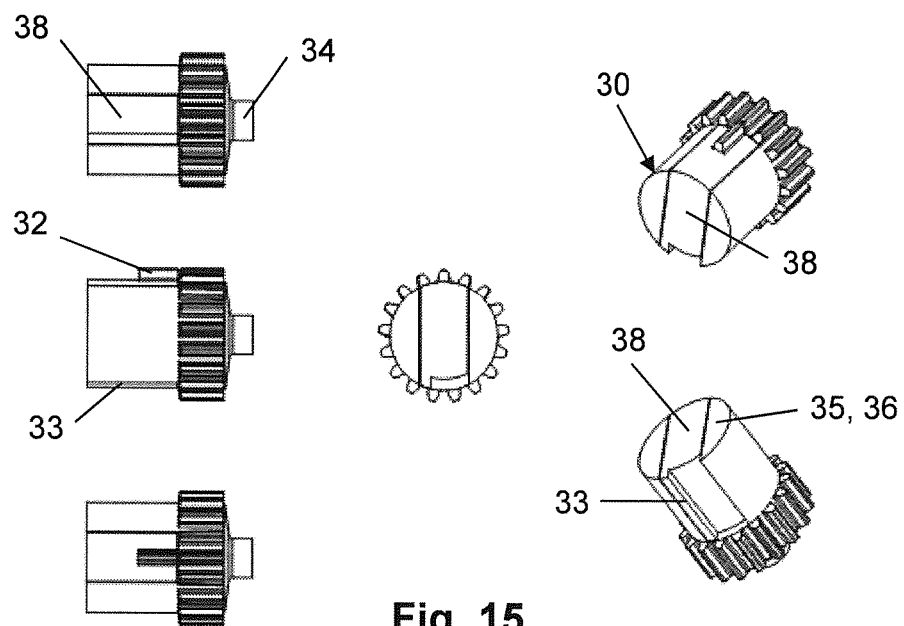
FIG. 15 is a front views and cross sections of the second limiting means in the third embodiment, in the form of a stop wheel with a transversely movable gearing means-guided second limit stop means.
Figure 18:
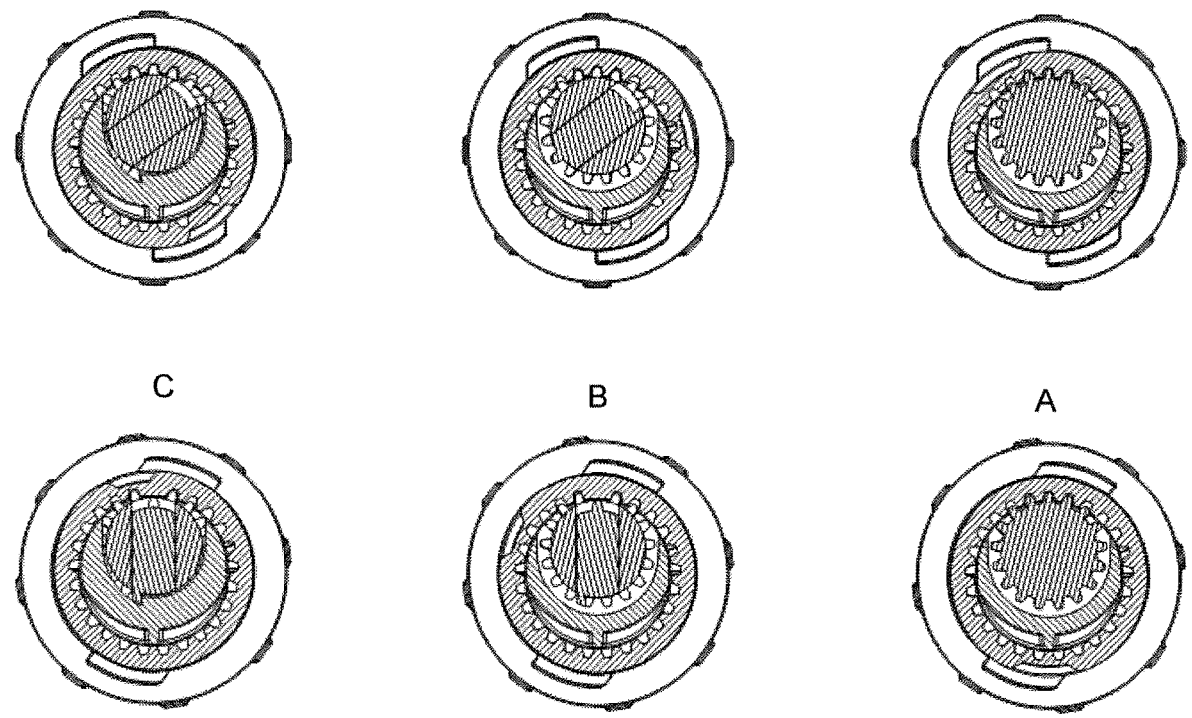
FIG. 18 is a cross sections of the limiting mechanism in the third embodiment in axial drive, stop and limit stop zones in a normal position and a stop position.

FIGS. 14-18 show a third embodiment of the device according to the invention installed as an example in an injection device similar to FIG. 1. FIGS. 14a and b show longitudinal sections of the limiting mechanism of the third embodiment in a normal position and in a stop position. FIG. 15 shows front views of the second limiting means in the third embodiment in the form of a stop wheel with a transversely movable second limit stop means and gearing means return. FIG. 16 shows a side view and a longitudinal section of the coupling sleeve in the third embodiment. FIG. 17 shows a side view and a cross section of the coupling sleeve in the third embodiment with a first limiting means and a gear cam. FIG. 18 shows cross sections of the limiting mechanism in the third embodiment in axial drive, stop and limit stop zones in a normal position and a stop position.

The application and function of the third embodiment correspond to the first embodiment apart from the following modifications made for the sake of example. The stop wheel 30 is designed with a rigid rotational shaft 36, the wheel and the shaft preferably being solidly integrated, and is rotatably received at the proximal shaft end 34 in the proximal bearing 42 and at its distal shaft end 35 in the distal bearing 43 of the coupling sleeve 40. In the area of the stop zone B and the limit stop zone C, a transverse guidance groove with inserted slider 38 retracted in its normal transversal position is provided in the rotational shaft 36 or in the stop wheel 30. In this normal position, the stop rib 32 on a face of the slider 38 can mesh with toothing 51 optionally formed in the area of the stop zone, so long as the stop rib 32 does not strike the stop wedge 52. If that is the case, the slider 38 is moved transversely to the rotational shaft against defined static and sliding frictional forces into its stop position. The counter-limit stop 33 formed on the side face of the slider 38 opposite the stop rib 32 as a second limit stop means is thereby brought into engagement with the limit stop 44 positioned as a first limit stop means on the coupling sleeve 40. The engagement prevents further rotation of the stop wheel 30 in the dosage-increasing direction. Conversely, this engagement is released in case of a rotation of the stop wheel 30 in the dosage-reducing direction. Then the stop rib 32 again detaches from the stop wedge 52, and the slider 38 is moved back into its normal position based on the transmission-like interaction of the counter-limit stop 33, on a side face of the slider 38 opposite from the stop rib 32, and the gear cam 45 in the coupling sleeve 40.

It is understood that the dosage limitation in all embodiments according to the invention also functions if the first and second limit stop means in the previous embodiments are omitted and the blocking of the rotational movement takes place only by the striking of first and second stop means.

An additional blocking mechanism can also be provided in all embodiments. When the last possible quantity of product to be administered has been ejected, i.e., when the cartridge 3 has been completely emptied, the conveying device blocks further ejection rotation of the dosing sleeve 50. In that case, the end 8a of the thread on the threaded rod 8 strikes against the ribs of the inside thread of the threaded nut 7 and prevents any further axial movement of the threaded rod 8 relative to the threaded nut 7. Because the threaded rod 8 is rotationally locked with respect to the housing, no common rotation of the threaded nut 7 and the threaded rod 8 is possible. Consequently, the dosing sleeve 50 is prevented from screwing in farther, so long as the rotational lock between the coupling 40 and the dosing sleeve 50 is maintained. If a higher dosage was set than the amount of product that remains, then the non-administered remaining quantity can be read off through the window on the dosing sleeve 50 in the blocked state. This remaining quantity would then have to be injected in another administration process with a spare injection device. This inconvenience is generally avoided, however, by the limiting device according to the invention and the injection device shown as an example. That is to say, the end 8a of the thread on the threaded rod 8 contacts the ribs of the inside thread of the threaded nut 7 at the earliest when the dosing sleeve 50 has reached and displayed the remaining amount "0" and the cartridge is nominally empty.

Figure 19A:
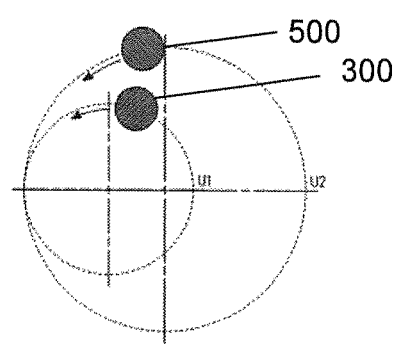
FIGS. 19a and b are arrangements of the first through third embodiments.
Figure 19B:
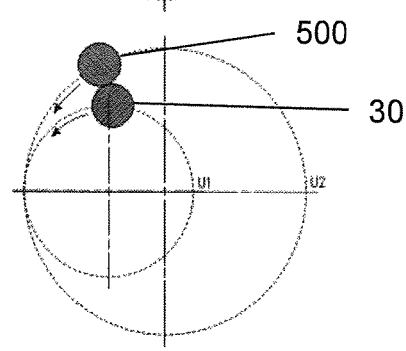

In general, the previously presented embodiments of the invention can be viewed as representatives of an arrangement as shown in FIGS. 19a and 19b. The stop means 300, 500 in this case move at the same speed, operatively connected in a form-fit to one another, on circular paths U1, U2 of different sizes, the axis of the smaller circle U1 lying inside the larger circle U2.

Figure 20A:
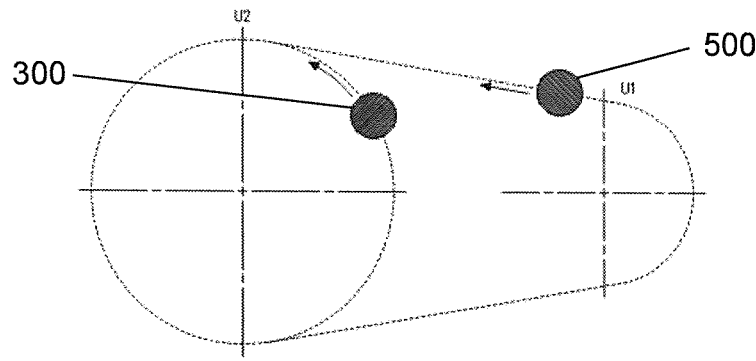
FIGS. 20a and b are arrangements of a fourth embodiment.
Figure 20B:
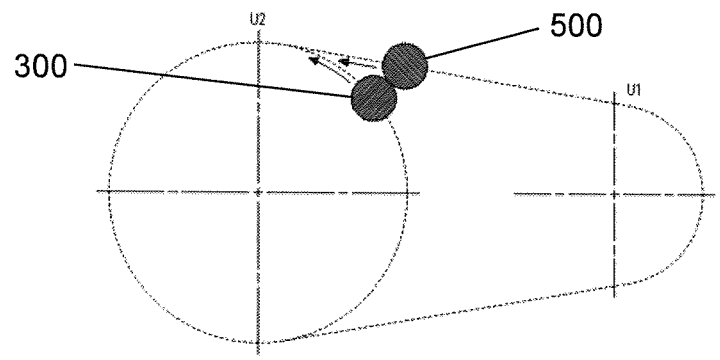

Representatives of an arrangement as shown in FIGS. 20a and 20b can be considered a fourth embodiment. At least one of the two stop means 300, 500 here moves on a non-circular closed path U1, as can be realized, for example, by a traction chain or toothed belt, or in general by a positively drivable closed belt or traction means. Such a traction means can advantageously be at least partially folded and/or reversed and/or located in a magazine in order to save space.

Figure 21A:
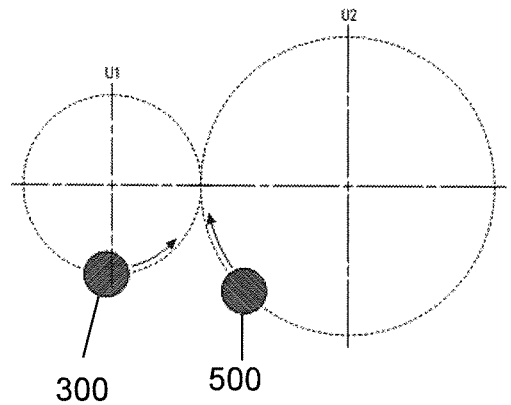
FIGS. 21a and b are arrangements of a fifth embodiment.
Figure 21B:
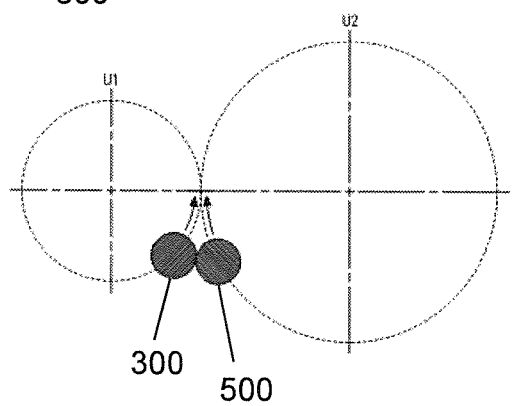

Representatives of an arrangement as shown in FIGS. 21a and 21b can be considered a fifth embodiment. The stop means 300, 500 in this case move at the same speed, operatively connected positively to one another, on circular paths U1, U2 of different sizes, the axis of the smaller circle U1 lying outside the larger circle U2.

Figure 22A:
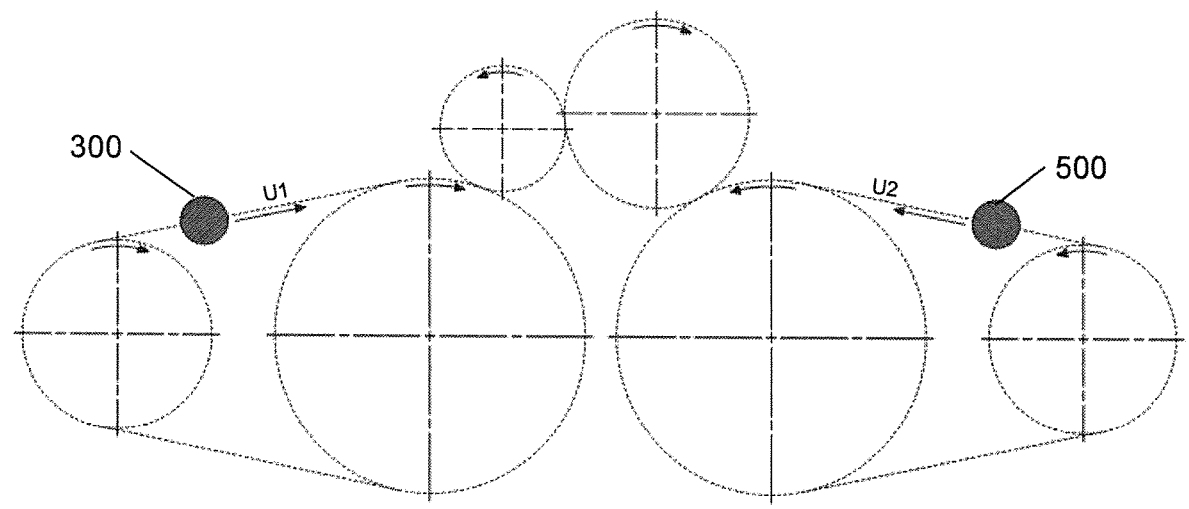
FIGS. 22a and b are arrangements of a sixth embodiment.
Figure 22B:
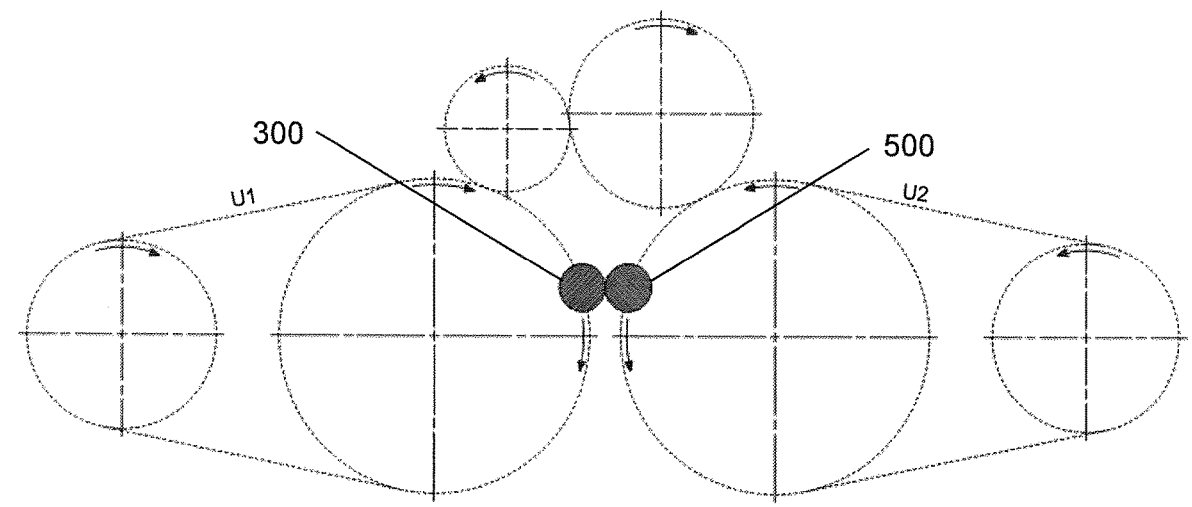

Representatives of an arrangement as shown in FIGS. 22a and 22b can be considered a sixth embodiment. The stop means 300, 500 here move with different speeds, operatively connected positively via a transmitting gear unit, on two equal-sized or different-sized closed paths U1, U2, as can be realized for example by traction chains or toothed belts or generally by positively drivable closed belts or traction means. Such traction means can advantageously be at least partially folded and/or reversed and/or located in a magazine in order to save space.

Figure 23A:
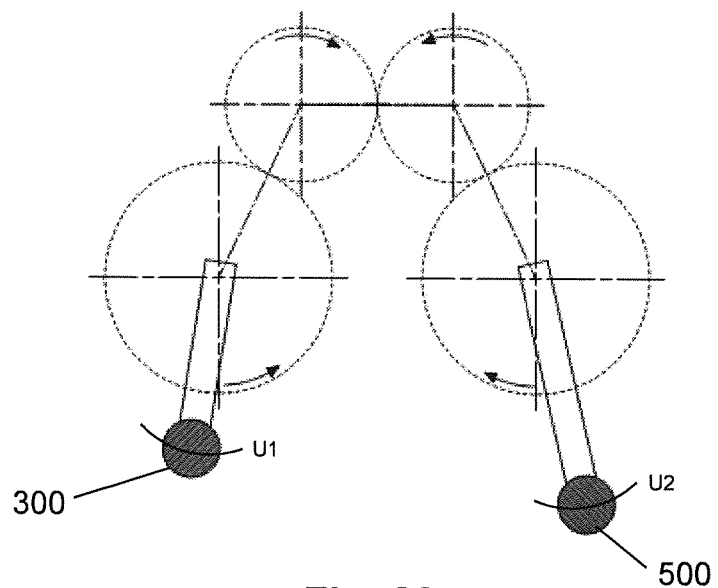
FIGS. 23a and b are arrangements of a seventh embodiment.
Figure 23B:
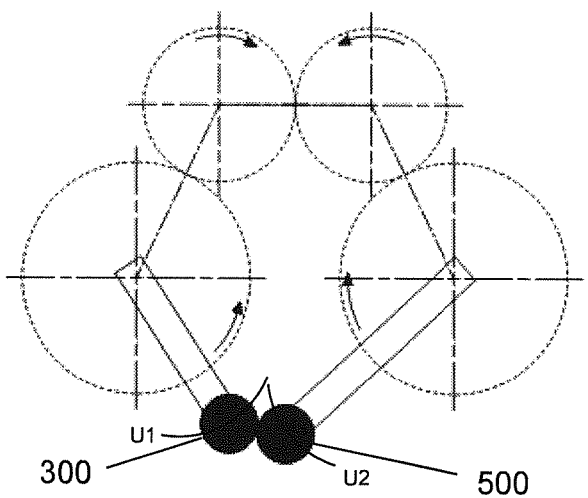

Representatives of an arrangement as shown in FIGS. 23a and 23b can be considered a seventh embodiment. In this case, the stop means 300, 500 move on rotatable guide means with different speeds operatively connected positively via a transmitting gear unit; shown only schematically in the figure, on two equal-sized or different-sized circular paths U1, U2, the axis of the one circle U1 lying outside the axis of the other circle U2.

What is claimed is:

1. A dosing device for an administration device with a limiting mechanism, comprising:
   a first limiting stop,
   a second limiting stop,
   wherein the second limiting stop proportionally follows movements of the first limiting stop during dosing,
   wherein the second limiting stop does not move relative to the first limiting stop during administration processes, and
   wherein each of the first limiting stop and the second limiting stop describes a path by its respective movements in such a manner that the two respective paths intersect in at least one point or come so close together that the first limiting stop and the second limiting stop contact one another in a stop position, whereby a blocking of the movement of the first limiting stop and the second limiting stop relative to each other during dosing movements is effected,
   wherein at least one of the respective paths described by the first limiting stop and the second limiting stop is run through multiple times until the first limiting stop and the second limiting stop contact one another at the stop position.

2. A dosing device according to claim 1, further comprising:
   a sleeve-like dosing member with an inner wall, an outer wall and a central axis, wherein at least one of the first limiting stop and the second limiting stop is constructed as a wedge or rib on the inner wall.

3. The dosing device of claim 2 wherein at least one of the first limiting stop and the second limiting stop is directly connected to the dosing member.

4. The dosing device of claim 3 wherein at least one of the first ng stop and the second limiting stop is fixedly connected to the dosing member.

5. The dosing device according to claim 2 wherein at least one of the first limiting stop and the second limiting stop forms a unitary part of the dosing member.

6. The dosing device of claim 2 wherein at least one of the first limiting stop and the second limiting stop is on an inner axial wall of the dosing member.

7. The dosing device of claim 6 wherein at least one of the first limiting stop and the second limiting stop is located at an end section of the dosing member.

8. The dosing device of claim 7 wherein at least one of the first limiting stop and the second limiting stop extends towards the central axis of the dosing member, thereby partially reducing the inner diameter of the dosing member.

9. The dosing device of claim 8 wherein at least one of the first limiting stop and the second limiting stop is oriented parallel to the central axis of the dosing member.

10. The dosing device according to claim 9 wherein the first limiting stop is constructed as a wedge or rib on the inner axial wall.

11. The dosing device according to claim 1, further comprising a coupling device for coupling the dosing device to an administration device, wherein the coupling device comprises a coupling sleeve coaxially arranged within a dosing sleeve of the dosing device, the coupling sleeve having a coupling surface with engagement elements that are connectable in a coupling engagement with a counter coupling surface having counter engagement elements on the dosing sleeve.

12. The dosing device according to claim 11 wherein the coupling sleeve is couplable to a housing of the administration device by a reverse lock.

13. The dosing device according to claim 11 wherein the coupling sleeve is rotationally secured and axially moveable relative to a drive element of the administration device.

14. The dosing device according to claim 11 wherein the coupling engagement between the coupling sleeve and the dosing sleeve is created by pressing an ejection button.

15. The dosing device according to claim 14 wherein the ejection button is coaxially mounted with the dosing sleeve and the ejection button is rotatable with respect to the dosing sleeve.

16. The dosing device according to claim 11 wherein the coupling surface is arranged on an annular flange in a proximal area of the coupling sleeve.

17. The dosing device according to claim 11 wherein the dosing sleeve is rotatable with respect to the coupling sleeve during a dose setting and wherein the dosing sleeve is coupled to rotate with the coupling sleeve during a dose delivery.

18. The dosing device according to claim 11 wherein at least one of the first limiting stop and the second limiting stop is directly or indirectly coupled to the coupling sleeve.

19. An administration device comprising the dosing device according to claim 1 wherein the administration device is a single use pen device.

20. The administration device according to claim 19 wherein a set product dosage is displayed in a window of the administration device.

21. The administration device according to claim 19 further comprising a kinematic arrangement between a piston rod and a drive element of the administration device and such arrangement comprises a threaded engagement.

22. The administration device according to claim 21 wherein a set product dosage is ejected from a receptacle of the administration device by a conveyance stroke of the piston rod that corresponds to the set product dosage, displacing a moveable piston in the receptacle.

* * * * *

UNITED STATES PATENT AND TRADEMARK OFFICE
CERTIFICATE OF CORRECTION

PATENT NO. : 11,058,822 B2  
APPLICATION NO. : 16/867041  
DATED : July 13, 2021  
INVENTOR(S) : Jürg Hirschel and Ulrich Moser Page 1 of 1

It is certified that error appears in the above-identified patent and that said Letters Patent is hereby corrected as shown below:

In the Claims

In Column 13, Line 38, Claim 4 delete ""ng"" and replace with --limiting--

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*